United States Patent
Schmitt

[11] Patent Number: 6,042,592
[45] Date of Patent: Mar. 28, 2000

[54] THIN SOFT TISSUE SUPPORT MESH

[75] Inventor: Peter J. Schmitt, Garnerville, N.Y.

[73] Assignee: Meadox Medicals, Inc., Oakland, N.J.

[21] Appl. No.: 08/905,529

[22] Filed: Aug. 4, 1997

[51] Int. Cl.⁷ .................................................. A61B 17/00
[52] U.S. Cl. ........................................................... 606/151
[58] Field of Search .................................. 606/198, 151, 606/154, 195, 192, 108, 191, 200, 213; 623/1, 11, 12; 604/365

[56] References Cited

U.S. PATENT DOCUMENTS

| | | |
|---|---|---|
| 2,671,444 | 3/1954 | Pease, Jr. . |
| 3,054,406 | 9/1962 | Usher ........................................ 606/151 |
| 3,063,454 | 11/1962 | Coates et al. . |
| 3,124,136 | 3/1964 | Usher . |
| 3,272,204 | 9/1966 | Artandi et al. . |
| 3,372,696 | 3/1968 | Rudie . |
| 3,376,869 | 4/1968 | Borysko . |
| 3,416,524 | 12/1968 | Meier . |
| 3,448,595 | 6/1969 | Baltzer et al. . |
| 3,526,228 | 9/1970 | Lyng . |
| 3,642,565 | 2/1972 | Ogata et al. ............................. 161/173 |
| 3,849,044 | 11/1974 | Ando et al. ........................... 425/131.5 |
| 4,205,668 | 6/1980 | Criddle . |
| 4,347,847 | 9/1982 | Usher . |
| 4,452,245 | 6/1984 | Usher . |
| 4,520,821 | 6/1985 | Schmidt et al. . |
| 4,542,739 | 9/1985 | Schäfer et al. . |
| 4,626,253 | 12/1986 | Broadnax, Jr. . |
| 4,633,873 | 1/1987 | Dumican et al. . |
| 4,693,720 | 9/1987 | Scharnberg et al. . |
| 4,769,038 | 9/1988 | Bendavid et al. . |
| 4,838,884 | 6/1989 | Dumican et al. . |
| 4,854,316 | 8/1989 | Davis . |
| 4,921,704 | 5/1990 | Fabo . |
| 5,019,096 | 5/1991 | Fox, Jr. et al. ............................... 623/1 |
| 5,100,422 | 3/1992 | Berguer et al. . |
| 5,116,357 | 5/1992 | Eberbach . |
| 5,122,155 | 6/1992 | Eberbach . |
| 5,141,515 | 8/1992 | Eberbach . |
| 5,147,374 | 9/1992 | Fernandez . |
| 5,176,692 | 1/1993 | Wilk et al. . |
| 5,178,630 | 1/1993 | Schmitt . |
| 5,195,542 | 3/1993 | Gazielly et al. . |
| 5,201,745 | 4/1993 | Tayot et al. . |
| 5,234,457 | 8/1993 | Andersen ................................. 606/198 |
| 5,254,133 | 10/1993 | Seid . |
| 5,263,969 | 11/1993 | Phillips . |
| 5,290,217 | 3/1994 | Campos . |
| 5,292,328 | 3/1994 | Hain et al. .............................. 606/151 |
| 5,358,492 | 10/1994 | Feibus ..................................... 604/264 |
| 5,366,460 | 11/1994 | Eberbach . |
| 5,368,602 | 11/1994 | de la Torre . |
| 5,370,650 | 12/1994 | Tovey et al. . |
| 5,383,477 | 1/1995 | DeMatteis . |
| 5,549,967 | 8/1996 | Gstein ..................................... 428/229 |
| 5,634,931 | 6/1997 | Kugel . |

FOREIGN PATENT DOCUMENTS

| | | |
|---|---|---|
| 0 625 417 A1 | 11/1994 | European Pat. Off. . |
| 0 692 225 A2 | 1/1996 | European Pat. Off. . |
| 725343 | 3/1955 | United Kingdom . |
| WO94/27535 | 12/1994 | WIPO . |
| WO97/22310 | 6/1997 | WIPO . |

Primary Examiner—Michael Buiz
Assistant Examiner—Vikki Trinh
Attorney, Agent, or Firm—Hoffman & Baron, LLP

[57] ABSTRACT

A soft and pliable surgical support mesh exhibiting increased resistance to inhabitation of infectious matter. The mesh includes a support trellis formed of multifilament yarns wherein the interstitial voids located between the filaments of said yarns are enclosed within an infection-impervious matrix. The meshes may be designed to be extremely thin yet retain the requisite strength for repairing soft tissue, which allows for a low profile when folded for delivery.

29 Claims, 7 Drawing Sheets

THIN SOFT TISSUE SUPPORT MESH

BACKGROUND OF THE INVENTION

The present invention relates to a surgical mesh and, more particularly, to a soft and pliable multifilament surgical support mesh exhibiting improved resistance to inhabitation of bacteria and other infectious matter.

Using surgical mesh for the repair and restoration of living tissue is well known. For example, surgical mesh may be used to support and/or reinforce a damaged or weakened portion of the body. In this regard, the mesh must additionally be sufficiently porous to allow for growth of tissue through the graft after implantation. The healing tissue grows through porous openings in the implanted mesh, thereby assimilating the mesh and adding structural integrity to the tissue.

Surgical mesh may be produced by knitting, weaving, braiding, or otherwise forming a plurality of yarns into a support trellis. Moreover, such mesh may be produced with monofilament or multifilament yarns made of materials such as polypropylene and polyester. Surgical mesh formed of monofilament yarn provides satisfactory reinforcement ability, but is generally stiff and has limited pliability. In contrast, surgical mesh formed of multifilament yarn is soft and pliable in comparison to mesh formed of monofilament yarn.

However, mesh formed of multifilament yarn may tend to harbor infectious matter such as bacteria. Particularly, the small void areas or interstitial spaces between the filaments of a multifilament yarns may promote the breeding of such bacteria. To date, surgeons typically prefer the monofilament design because of its improved resistance to harboring of infectious matter. As a result of this choice, surgeons must forego the advantages associated with multifilament yarns.

An example of a prior art surgical mesh is disclosed in U.S. Pat. No. 2,671,444. The surgical mesh described therein is an integral network of interconnecting yarns formed by molding a polyethylene resin. In essence, the '444 mesh is a molded, monofilament mesh and, hence, is relatively stiff and exhibits limited pliability.

U.S. Pat. No. 3,054,406 discloses another example of a surgical mesh used for repair and restoration of living tissue. The surgical mesh described therein may be woven from either monofilament or multifilament polyethylene yarns. The mesh has limited pliability when formed of monofilament yarns, and may be prone to harboring of infectious matter when formed of multifilament yarns.

U.S. Pat. No. 4,452,245 discloses still another example of a surgical mesh. The surgical mesh described therein is formed with monofilament polypropylene yarns which are knitted into a continuous tubular shape. The knitted mesh is porous and exhibits infection-resistant characteristics because of its monofilament construction. However, the monofilament mesh tends to be stiff and relatively non-pliable, which detracts from the body's ability to incorporate the mesh.

Surgical support mesh has been extremely useful in the field of repairing soft tissue such as during a hernia repair operation. Groin herniorrhaphy is among the oldest and most common surgical procedures performed. Unfortunately, the average operative result is beset by a period of discomfort with resultant disability. Techniques have been developed, such as laparoscopic herniorrhaphy, with the intent to reduce morbidity and recurrence rates. Most trials, however, have noted only a moderate improvement in the pain and disability associated with the procedure. Further, the added cost of equipment, the need for general anesthesia, and the additional operating room time required for laparoscopic herniorrhaphy indicates that this procedure is less than ideal. There continues to be a need for a procedure that can effectively address all the considerations of cost, disability, and hernia recurrence for patients with an inguinal hernia.

While the placement of a prosthetic mesh in the properitoneal space is currently performed with either a laparoscopic or an open technique, it is desirable to perform the procedure through even less invasive means. One such means contemplated involves the use of needles to deliver the mesh into the peritoneal cavity. Delivery of mesh by means of a needle, however, has heretofore not been possible in part due to the unavailability of mesh which is thin enough to be passed through the cannula of a needle, yet of sufficient strength and flexibility to adequately serve its intended purpose.

There is therefore a need for a soft tissue surgical mesh which can be made having a thickness that allows the mesh to be rolled or folded and thereafter inserted into the cannula of a needle for deployment in the body and which exhibits both the soft and pliable characteristics of a mesh produced from multifilament yarns and the infection resistance of a mesh produced from monofilament yarns. The mesh should also be non-linting, fray resistant, and ravel resistant.

SUMMARY OF THE INVENTION

The present invention, which addresses the needs of the art, provides a soft and pliable surgical mesh. The mesh includes a support trellis formed of multifilament yarns encapsulated within an infection-impervious matrix whereby the interstitial voids located between the filaments of the yarns are enclosed within the matrix. The matrix also imparts a requisite degree of ravel resistance to the mesh wherein the yarns will be prevented from shifting or separating. The mesh may be composed of fine multifilament yarns in a knitted or woven construction that would possess the desired mechanical strength and porosity for use in tissue repair or reinforcement.

The present invention also provides a method of producing a soft and pliable surgical mesh exhibiting increased resistance to inhabitation of infectious matter from a support trellis formed of multifilament yarns. The method includes the step of encapsulating the multifilament yarns within an infection-impervious matrix whereby the interstitial voids located between the filaments of the yarns are enclosed within the matrix. In one embodiment the fabric is made very thin to facilitate delivery through a minimally invasive device. The thickness of the fabric is tailored to the specific application and delivery apparatus. Such techniques as pressing or calendaring of the yarns in the finishing-off operation using heat and/or pressure to compress the fabric to the desired thickness may also be employed.

The present invention provides a mesh fabric that is designed to be particularly useful in minimally invasive surgical procedures for repairing and/or reinforcing tissue, such as during hernia repair. Due to its thin profile, the mesh fabric may be rolled or folded to occupy a sufficiently small volume to facilitate its introduction and delivery into the body using such devices as trocars, cannulas and the like. The mesh may also have an elastic memory imparted thereto so as to return to the desired configuration once removed from the delivery device. For example, the mesh may be designed to unfurl and assume a relatively planar configuration once deployed from the delivery device.

The present invention also provides a method of repairing a damaged portion of a patient's body. The method includes the step of providing a soft surgical mesh. In some applications the mesh may further be rolled, folded, or otherwise compressed in size to fit within the cannula of a laparoscopic delivery device. The mesh of the present invention includes a support trellis formed of multifilament yarns encapsulated within an infection-impervious matrix whereby the mesh is soft and pliable while simultaneously exhibiting a resistance to inhabitation of infectious matter. The method includes the further steps of accessing the damaged portion of the body, implanting the surgical mesh in the body to reinforce the damaged portion, and allowing the mesh to assimilate into the body.

As a result, the present invention provides a surgical support mesh which exhibits both the soft and pliable characteristics of a mesh produced from multifilament yarns and the infection resistance of a mesh produced from monofilament yarns. Moreover, the present invention provides a surgical support mesh which is non-linting, fray resistant, and ravel resistant. Further still, the mesh of the present invention may be formed with an appropriate thickness so as to be delivered into a peritoneal cavity via a laparoscopic device.

DETAILED DESCRIPTION OF THE INVENTION

Figure 1:
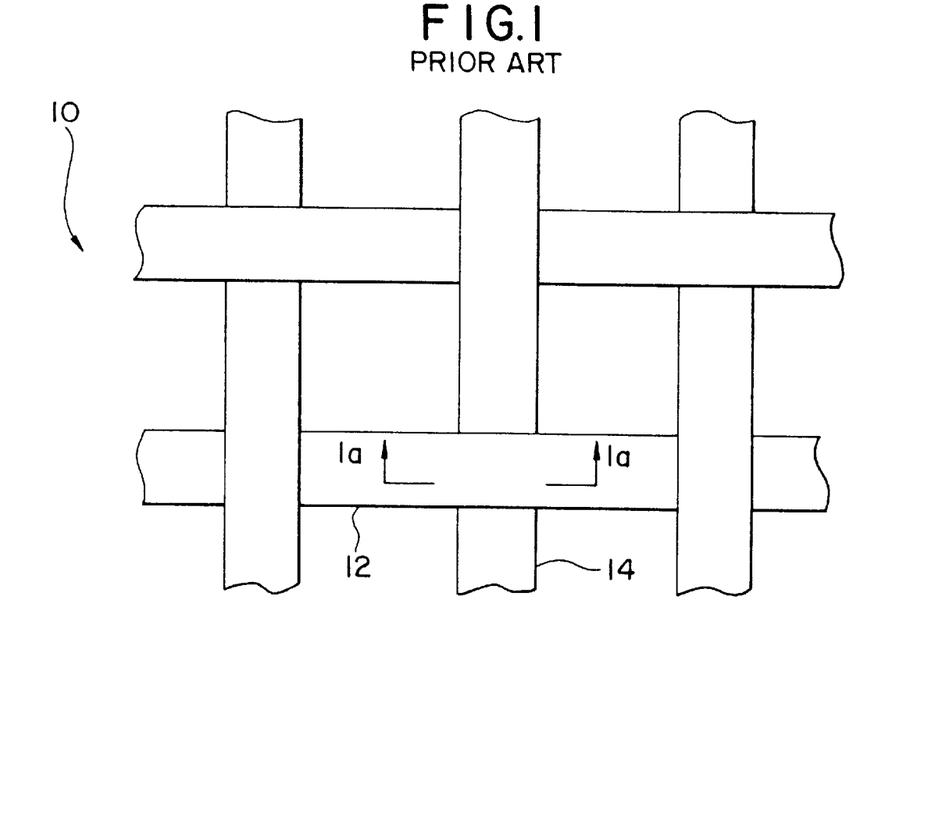
FIG. 1 shows a portion of a woven prior art support mesh made of multifilament yarns.

Referring to the drawings and, in particular to FIG. 1, therein illustrated is a prior art surgical support mesh 10. Mesh 10 may be manufactured from monofilament or multifilament yarns. Prior art mesh 10, as shown, includes multifilament horizontally-extending yarns 12 and multifilament vertically-extending yarns 14 woven together to form a support trellis.

The use of multifilament yarns, such as yarns 12 and 14, provides a mesh having greater pliability and suppleness than the use of monofilament yarns. These characteristics result from both the smaller diameter of the individual filaments and the interstitial spaces or voids that are located between such filaments.

In particular, the flexibility of a filament (or fiber) generally increases as its diameter decreases. Because the solid cross-sectional area of the filaments of a multifilament yarn is less than the cross-sectional area of a monofilament yarn of equivalent diameter, the multifilament yarn will have a greater degree of flexibility and pliability than that of the monofilament yarn.

Figure 1A:
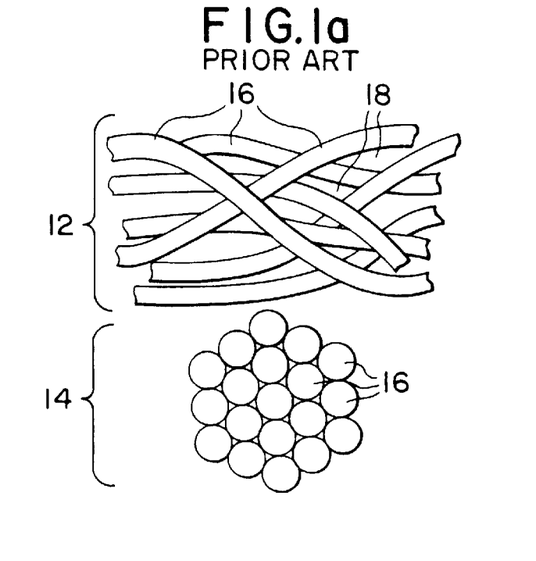
FIG. 1a is a sectional view taken along lines 1a—1a of FIG. 1.

As shown in FIG. 1a, each of multifilament yarns 12 and 14 is composed of a plurality of filaments 16 that are intermingled or bundled together to form the yarn. Interstitial spaces 18, which are pockets of air, are formed between adjacent filaments of the yarn. Although these voids contribute to the softness and pliability of the formed mesh, they also provide a natural breeding ground for bacteria or other infectious material.

Surgical mesh is, of course, thoroughly sterilized prior to implantation. Nevertheless, surgeons typically prefer the use of monofilament-designed mesh to minimize any risk of infection. As a result, the advantages associated with multifilament-designed mesh (i.e., softness and pliability which result in better assimilation of the mesh into the body) are typically sacrificed.

It has been discovered herein that a surgical support mesh having both the softness and pliability of a multifilament-designed mesh and the infection resistance of a monofilament-designed mesh may be produced. Particularly, it has been discovered that a support trellis formed of multifilament yarn wherein the interstitial voids located between adjacent filaments are enclosed within an infection-impervious matrix exhibits the desired resistance to harboring of infectious matter without significant loss of flexibility.

Particularly, the matrix, which completely encloses the interstitial voids between the filaments of the yarn, provides an effective barrier to the passage of infectious matter between the interior and exterior of the yarn. Accordingly, any voids remaining in the yarn after encapsulation of such yarn are enclosed (and thereby sealed) within the resultant matrix.

Figure 2:
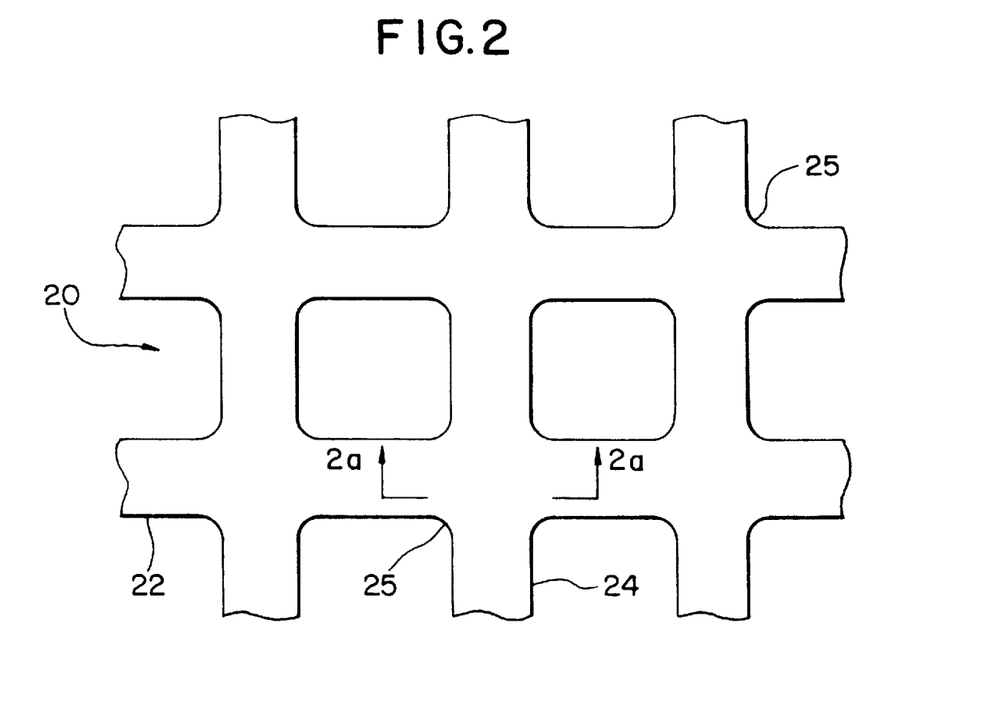
FIG. 2 shows a portion of a support mesh of the present invention wherein a woven support trellis formed of multifilament yarns has been encapsulated within an infection-impervious matrix in accordance with the present invention.

A first embodiment of the present invention is shown in FIG. 2. Particularly, this first embodiment includes a support trellis 20 formed of multifilament yarns 22 and 24 which overlap at cross-over junctions 25. Subsequent to forming of the trellis, such trellis is encapsulated within a matrix 26, which is preferably a flexible material that continuously surrounds the exterior of the yarns thereby enclosing interstitial voids 27 located between filaments 28 (see FIG. 2a). In one embodiment, the matrix is formed from a polymeric resin.

Figure 2A:
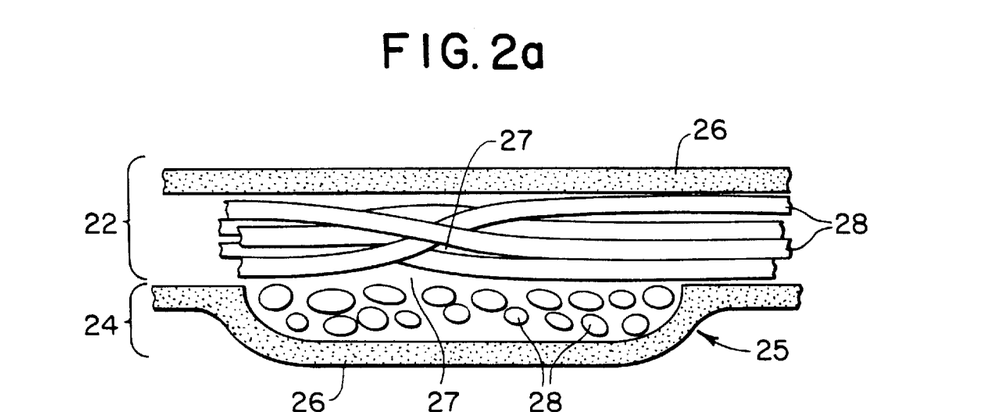
FIG. 2a is a sectional view taken along lines 2a—2a of FIG. 2.

As shown in FIG. 2a, the resin can be applied to the yarn in such a manner as to not allow the resin to substantially penetrate into the yarn. Particularly, the penetration of the resin can be controlled through the application procedure, e.g., quantity of resin applied and/or encapsulating time. In such an embodiment, the interstitial spaces are enclosed (rather than filled) within the continuous matrix. However, it is contemplated that the resin can be allowed to penetrate into the yarn, thereby substantially filling the void space located therein.

Figure 3:
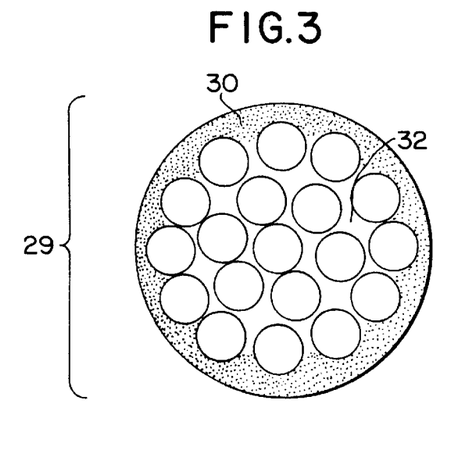
FIG. 3 is a sectional view of a multifilament yarn which has been encapsulated within an infection-impervious matrix prior to forming of the support trellis.
Figure 3A:
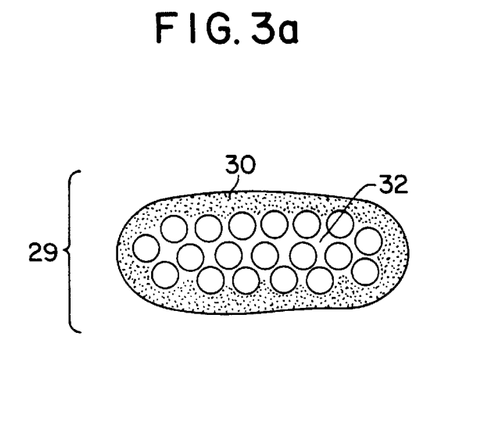
FIG. 3a is a sectional view of the multifilament yarn of FIG. 3 having its thickness reduced in accordance with the present invention.

In another embodiment of the present invention, individual yarns 29, as shown in FIG. 3, are encapsulated within matrix 30 prior to forming of the support trellis. FIG. 3a shows a compressed yarn 29 which provides a trellis having a reduced thickness. As a result of the encapsulation, interstitial voids 32 remaining in the yarn are enclosed (and thereby sealed) within the matrix. This then prevents infectious matter from traveling between the interior and exterior of the yarn. Stated differently, the matrix provides an infection-impervious barrier between any interstitial voids remaining in the yarn after encapsulation and the exterior of such yarn, while simultaneously maintaining the desired flexibility.

Figure 4:
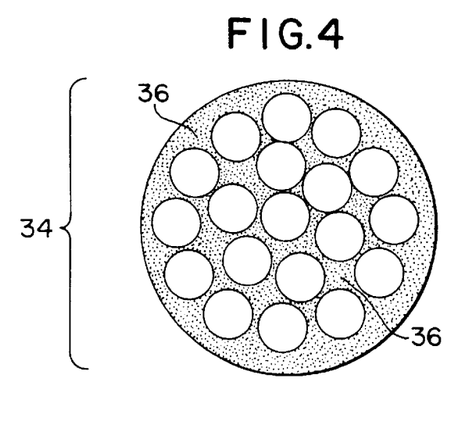
FIG. 4 is a view similar to FIG. 3, wherein the encapsulating resin which forms the matrix has penetrated into the yarn and has substantially filled the interstitial voids.
Figure 4A:
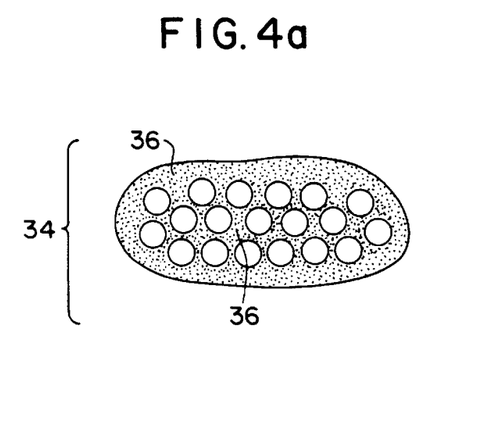
FIG. 4a is a sectional view of the multifilament yarn of FIG. 4 having its thickness reduced in accordance with the present invention.

As mentioned, the depth of penetration of the matrix can be controlled by regulating the quantity of resin applied to the yarn and/or by regulating the coating time. For example, referring to yarn 34 shown in FIG. 4 and FIG. 4a, matrix 36 penetrates into the interstitial spaces of the yarn, thereby substantially filling the bulk of air space located therein.

The resin employed to encapsulate the trellis preferably has a melting temperature lower than the melting temperature of the individual filaments such that the resin may be applied to the trellis without damage thereto (i.e., melting of the filaments). Moreover, the resin should exhibit a high degree of flexibility to ensure that the formed mesh retains its desired pliability. Preferably, the resin has a Young's Modulus lower than that of the filament material. Resins formed from polyester, polypropylene, polyethylene, polyurethane, poly(meth) acrylate, or copolymers thereof are contemplated for use herein.

In one embodiment of the present invention, a resin solution is applied to the formed trellis. The solvent carrying the resin is then caused to be evaporated, whereby the solute impregnates and thereby fills the voids within the yarn.

The encapsulation of the multifilament yarns permanently encloses the interstitial spaces formed between the individual filament of the yarns. Particularly, a continuous infection-impervious matrix is formed around the exterior of the yarn, thereby encapsulating the filaments and filling and/or sealing the interstitial spaces formed therebetween. The resultant surgical mesh therefore exhibits more softness and pliability than a monofilament yarn, while simultaneously providing a barrier to the passage of infectious matter, which infectious matter is common in conventional multifilament yarns.

Moreover, the encapsulation of the yarns, if done subsequent to forming of the support trellis, i.e. to the fabric per se, fuses the yarns of the trellis together at the crossover junctions 25 shown in FIG. 2. This improves the ravel resistance of the formed mesh. It also improves the linting and fraying characteristics of the mesh (i.e., the mesh is less prone to both linting and fraying). If, however, the individual yarns are encapsulated prior to forming of the trellis, the trellis may still be heated after formation to fuse the yarn coatings together, thereby rendering such trellis ravel resistant.

Figure 5:
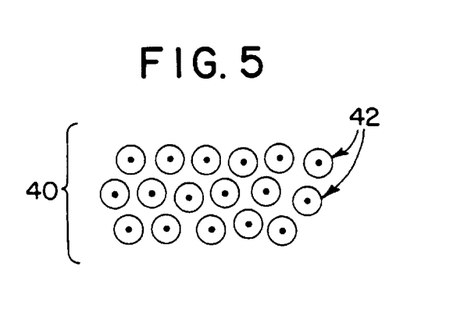
FIG. 5 is a sectional view of a multifilament yarn formed of bi-component fibers.
Figure 6:
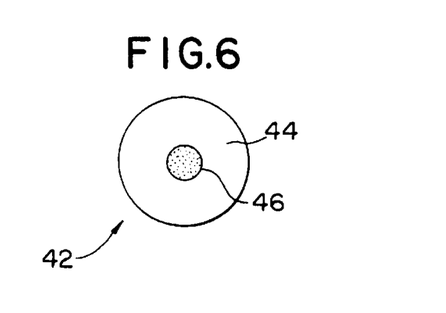
FIG. 6 is an enlarged sectional view of an individual bi-component fiber.

Referring to FIGS. 5 and 6, the multifilament yarns employed in the present invention, e.g., yarn 40, may be formed of bi-component filaments 42. Each of these bi-component filaments includes a sheath 44 and a core 46. The sheath is preferably formed of a material having a melting or fusing point lower than that of the material forming the core of the filament. Thus, when the filament is heated to a particular temperature, the sheath will soften and flow together with sheaths from adjacent filaments, thereby filling the void space between filaments and encapsulating the cores of such filaments. In another embodiment, where a means other than heat is used, for example, a liquid based coating material, once the solvent is evaporated the coating remains to encapsulate the filaments and/or filling the interstitial spaces formed therebetween.

The sheath 44 is preferably a polyethylene terephthalate/isophthalate co-polyester, while the core 46 is preferably a polyethylene terephthalate polyester. Of course, other suitable materials may be used to manufacture the bi-component filaments.

Figure 7:
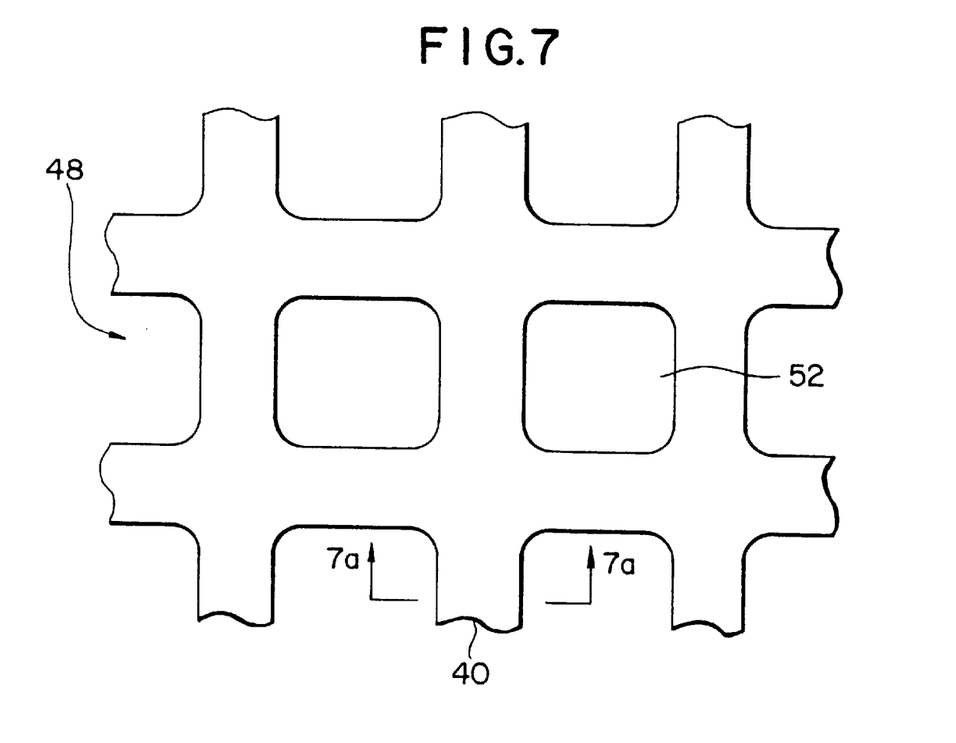
FIG. 7 shows a portion of a woven support mesh of the present invention formed of the bi-component multifilament yarns of FIG. 5 which have been fused following fabrication of the trellis.
Figure 7A:
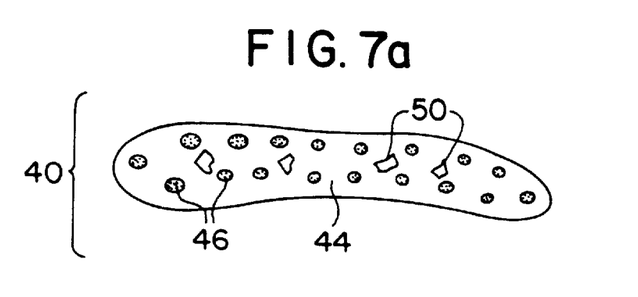
FIG. 7a is a sectional view taken along lines 7a—7a of FIG. 7.

Another embodiment of the present invention is shown in FIGS. 7 and 7a. Particularly, this embodiment includes a support trellis 48 formed of bi-component multifilament yarns, such as yarns 40. Subsequent to forming of the trellis, the trellis is heated to a predetermined temperature, i.e., the fusing temperature of the bi-component filaments.

It is at this fusing temperature that sheaths 44 of the bi-component filament begin to melt and flow together, thereby at least substantially filling the voids between filaments and also encapsulating cores 46 within a continuous polymeric matrix. The melting sheaths also enclose any voids 50 which are not filled by the flowing polymer. Because the polymer of sheath 44 is softer and more flexible than the polymer of core 46, the formed trellis exhibits the flexibility of a surgical support mesh which is closer to that formed of a conventional multifilament yarn than of a monofilament yarn. The component untwisted filament yarns also tend to flatten out. This flattening is emphasized even more due to transverse forces on the yarns during heat compression of the fabric. Additionally, the sheath polymer flowing into the interstitial voids between the multifilaments causes the reduction of air between the fibers, further contributing to the consolidation of the yarn bundle.

The surgical mesh of the present invention may be formed by weaving, knitting, braiding or otherwise forming a plurality of multifilament yarns into a support trellis structure. The multifilament yarns may be either traditional multifilament yarns or bi-component multifilament yarns. When formed of bi-component multifilament yarns, the support mesh may thereafter be subjected to thermal or light energy to fuse the filaments together. For example, the mesh may be placed in an oven and heated to a temperature of, for example, 180–210° C., and preferably 200–210° C. such that the sheaths of the individual filaments fuse together.

The encapsulation of the yarns, whether by coating or fusing of bi-component filaments, provides the trellis with a "membrane-like" feel, while also eliminating the fibrous properties of a warp-knitted structure. Moreover, the present invention allows the size of the trellis pores (e.g., pores 52 shown in FIG. 7) to be regulated. For example, the pore size (preferably about 50 microns or larger) can be regulated by controlling the quantity of resin applied to the exterior of the trellis. It is believed that regulation of pore size may facilitate assimilation of the trellis into the body.

In one preferred embodiment of the present invention, a medicinal substance (e.g., an antibiotic) is incorporated into the matrix encapsulating the yarns. The drug may be dispersed directly throughout the encapsulating resin or, alternatively, added to a plurality of separate carriers which in turn are dispersed throughout the encapsulating resin.

In another embodiment of the present invention, a thin mesh is formed having a thickness in the range of about 0.05 millimeters to about 0.50 millimeters. Preferably, the thin mesh of the present invention will have a thickness of about 0.10 millimeters to about 0.20 millimeters. The mesh width and length dimensions can vary within those ranges conventionally used for a specific application and delivery device. For example, such ranges include dimensions of about 12 centimeters×15 centimeters to about 14 centimeters×16 centimeters. These ranges are generally sufficient to cover the area of repair of, for example, the myopectineal orifice of an adult. As mentioned above, such a thin surgical mesh could then be rolled or otherwise folded so as to fit within the cannula of a needle having a small diameter of, for example, 5 millimeters or less.

In addition to the soft and pliable characteristics provided by multifilament yarns, the individual filaments or fibers are capable of spreading out or flattening to provide a reduced thickness and a low profile. To maximize the yarn's ability to splay it is necessary to minimize or prevent the introduction of twisting or other such orientations of the yarn which might impede its ability to adopt a low profile.

In creating a thin woven mesh in accordance with the present invention, attention must be given to the spacing of the threads (i.e. the end count) such that the openings defined by the weave construction are small and particularly on the order of about 50 to about 200 microns. Weave constructions made in this manner benefit from the use of bicomponent multifilament yarns since they provide the required mechanical properties to reinforce tissue. Moreover, a bicomponent yarn allows for one of the components to be a meltable resin which, when heated, subsequently can fuse together with other yarns in the fabric to weld at the interlacing points to seal the structure.

The welding of the interlaces stabilizes the yarns in the woven structure while the sealing of the yarns eliminates the porosity with the yarn bundle and thereby reduces the risk of harboring infections. The treatment also imparts a resiliency to the mesh to resume a planar shape once released from the cannula.

Multifilament yarns also can provide a lower profile to the mesh as they can flatten out. The flattening characteristic of multifilament yarn is maximized when the yarn is not impeded by twisting or other yarn conditioning. Once woven, the fabric is heat set which causes the yarn to assume an elliptical cross-section, rather than the round cross-section retained by a monofilament or a highly twisted multifilament yarn.

One embodiment of a thinly woven mesh of the present invention includes use of a 75 denier bicomponent polyester yarn having a circular diameter of, for example, about 0.09 millimeters. The multifilament yarns contemplated for use in the present invention can be flattened preferably about 50 percent of the original thickness. When flattened, the yarn assumes an elliptical or race-track (rectangular with rounded corners) cross-section having a minor diameter, or yarn thickness, of about 0.04 millimeters to about 0.06 millimeters, and a major diameter, or yarn width, of about 0.22 millimeters to about 0.28 millimeters. Using a square plain weave construction with 70 ends per inch by 70 picks per inch, or 28 ends per centimeters by 28 picks per centimeters, then the rectangular pore size would be about 0.05 to 0.07 millimeters on either or both sides, or 50 to 70 microns, respectively.

A woven construction provides a greater strength to thickness ratio than a knitted construction. It also allows the mesh to be engineered, for example, for isotropic or anisotropic properties more effectively, more predictably, and more thinly than a knitted fabric. The estimated burst strength of the fabric would be about 21 kg/cm$^2$, or 300 psi, or 2068 kPa. Such burst strengths are in the range of conventional surgical repair fabrics, including those for hernia repairs and which have a greater thickness than those contemplated by the present invention.

Additionally, the mesh may have a shape memory imparted thereto. The mesh could, for example, be heat conditioned for a sufficient time at a sufficient temperature while the mesh is in an unfurled configuration. The mesh could also include individual threads having a shape-memory imparted thereto, such as nitinol threads. The mesh could therefore be designed to assume an unfurled configuration when the mesh reaches body temperature subsequent to deployment. Imparting shape-memory to the mesh would allow the mesh, even after having been stored within the delivery device, e.g. the cannula of a needle, to assume an unfurled configuration once deployed into the peritoneal cavity. Designing shape-memory into the soft tissue mesh in this manner facilitates orientation in the body. Moreover, due to the encapsulating matrix, the mesh possesses a structural stability and ravel resistance which permits pulling and aligning using laparoscopic gripping devices.

Figure 8:
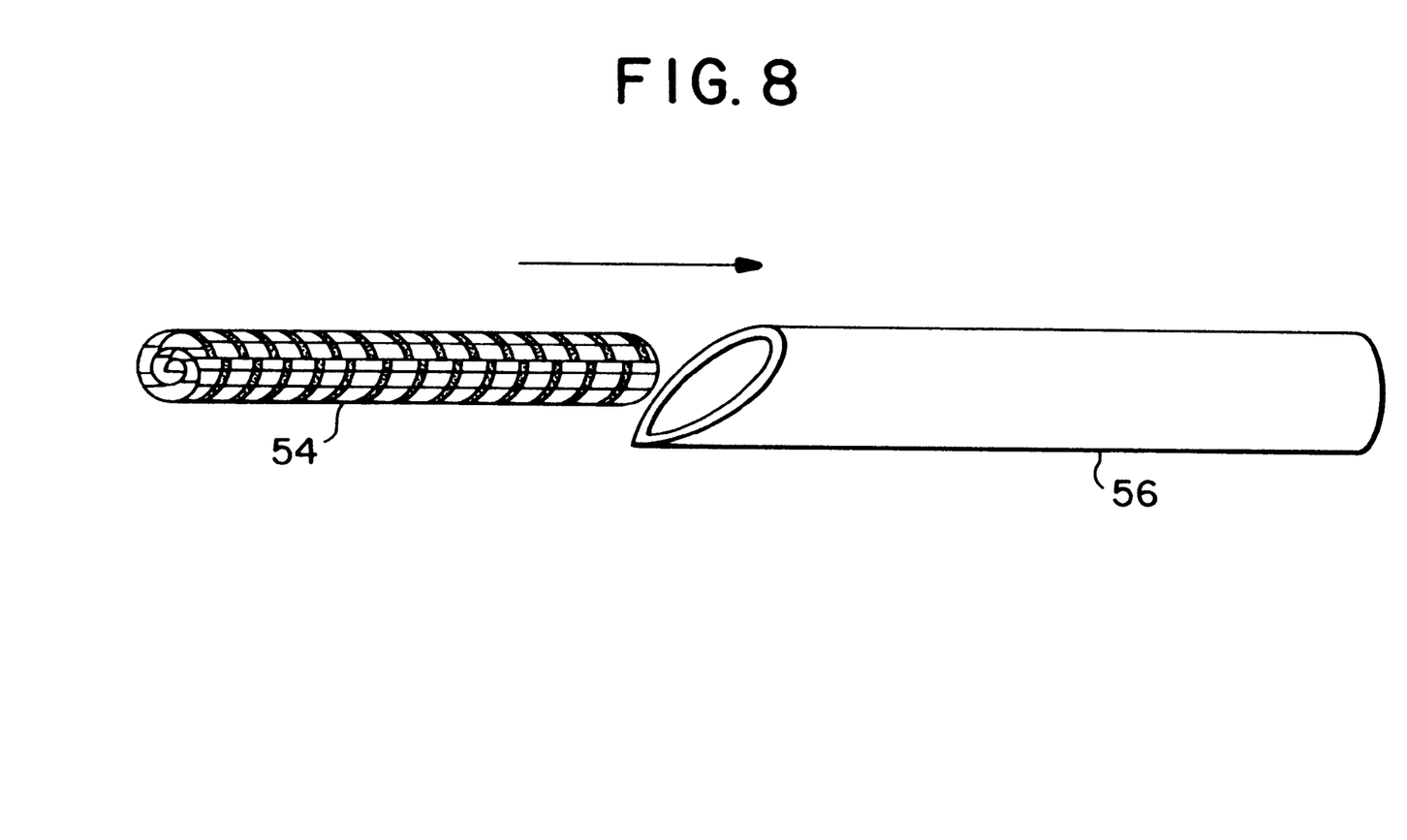
FIG. 8 is a view of a thin mesh of the present invention in a rolled position for insertion into the cannula of a needle.

The soft tissue meshes of the present invention may be implanted using conventional surgical or laparoscopic techniques. Preferably, a new minimally invasive technique employing a needle delivery is used. In such a method, the mesh is rolled, folded, or otherwise compressed to a reduced volume such that it can be contained within a needle delivery system. As shown in FIG. 8, rolled mesh 54 is shown being insertable into cannula 56. The mesh must have a sufficiently low volume and profile to pass through a needle cannula and be deployed into the affected area. Preferably, the mesh has been memory heat-set to return to a relatively planar configuration once deployed. Other shapes, depending on the specific body application may of course also be used. Once the mesh is expelled from the delivery system it is oriented and manipulated to the appropriate tissue site.

For example, thin surgical support mesh could then be delivered into the properitoneal cavity of a patient via the needle. A second small needle cannula could be inserted into the properitoneal cavity to insufflate the region with carbon dioxide. The hernia sac would be dissected free and ligated. Visualization during the needle herniorrhaphy would be obtained with a 2–5 millimeter laparoscope placed through one of the cannulas. The mesh, upon being expelled from the needle over the transversalis fascia, could then be manipulated to cover the myopectineal cavity. The mesh could further be provided with an elastic memory causing the mesh to unfurl once ejected from the cannula. The mesh may then be optionally sutured or stapled over the herniated region for assimilation by the body tissue so as to provide added support to the tissue of the properitoneal cavity.

A needle herniorrhaphy technique could therefore be performed which would obviate the need for open surgery. The needle herniorrhaphy technique could be performed without the need for general anesthesia and would reduce the pain and disability currently associated with open or laparoscopic techniques.

EXAMPLES

The following examples illustrate the surgical support mesh of the present invention.

Example 1

A support trellis is woven of bi-component yarns, particularly 250 denier/16 filament/type LHCV Kanebo Bellcouple® polyester yarns. The Kanebo Bellcouple® yarn includes a polyethylene terephthalate polyester core and a polyethylene terephthalate/isophthalate co-polyester sheath, the sheath having a lower melting temperature than the core.

Following construction of the support trellis, the trellis is placed in a convection oven and heated to about 210° C., thus fusing the individual sheaths together. The yarns are thereby encapsulated and, further, are fused to each other at the junctions where the yarns overlap.

The resultant mesh is thereafter sealed in a sterile package.

Example 2

A support trellis is warp-knitted of bicomponent yarns, particularly 75 denier/24 filament/type LHCV Kanebo Bellcouple® polyester yarns. Following construction of the support trellis, the trellis is placed in a convection oven and heated to about 210° C., thus fusing the individual sheaths together.

The resultant mesh is thereafter sealed in a sterile package.

Example 3

Figure 9:
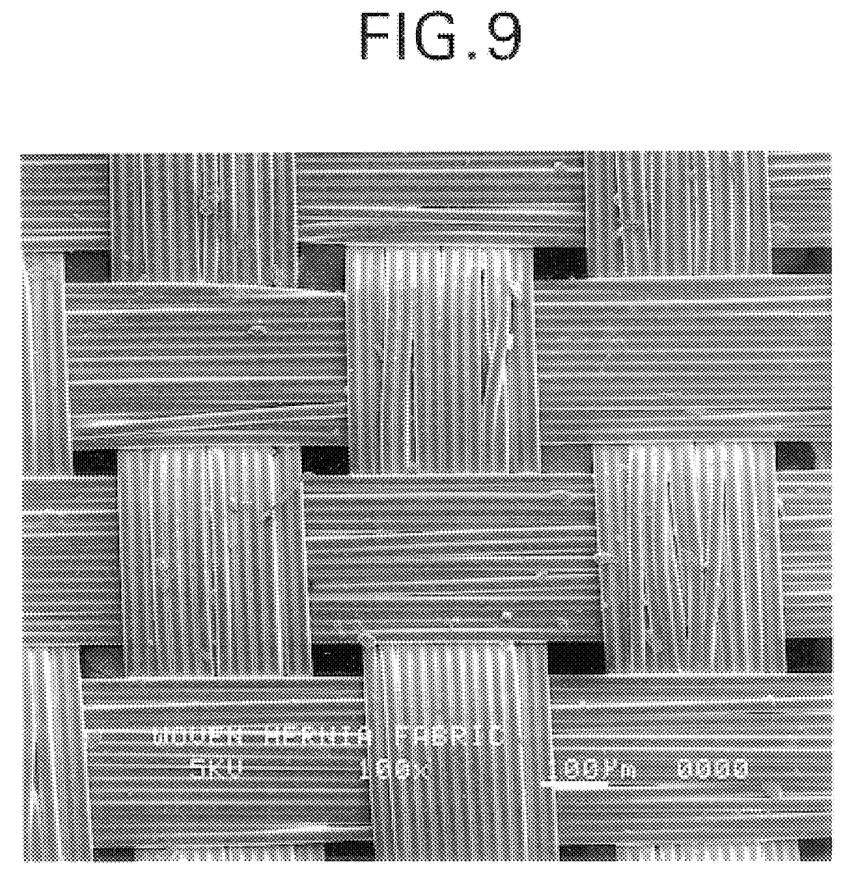
FIG. 9 is a photomicrograph of a portion of a mesh formed according to the present invention.
Figure 9A:
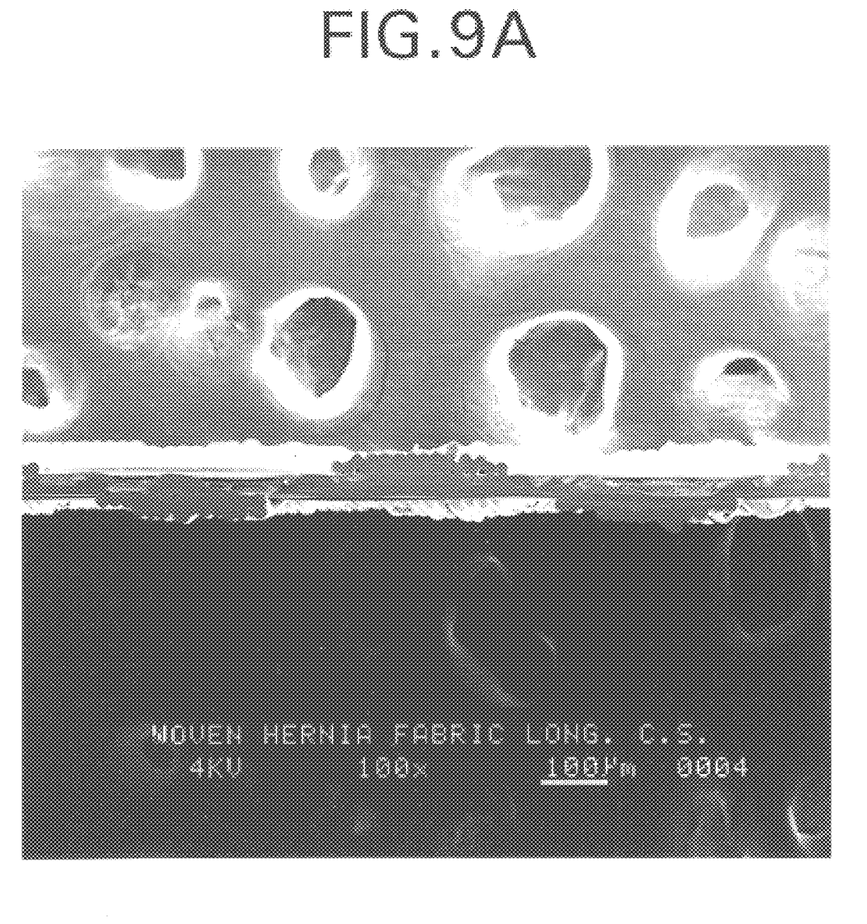
FIG. 9a is a photomicrograph showing a cross-sectional view of the mesh shown in FIG. 9.

A support trellis is woven in a plain weave of bicomponent yarns, particularly 75 denier/24 filament/type LHCV Kanebo Bellcouple® polyester yarns. The threadcount is 70 ends per inch by 70 picks per inch. The rectangular pore size is in the range of 50 to 70 micrometers on each side. Following construction of the support trellis, the trellis is placed in a forced hot air convection oven and heated to about 210° C. for 15 minutes, thus fusing the individual sheaths together. The thickness of the construction is on the order of 0.10 millimeters or less. FIG. 9 is a photomicrograph showing a portion of a construction according to this Example. FIG. 9a is a photomicrograph showing a cross-sectional view of this construction.

The resultant mesh is thereafter sealed in a sterile package.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A soft and pliable soft tissue mesh, comprising;
a support trellis formed of multifilament yarns having splayed filaments encapsulated within an infection-impervious matrix whereby each multifilament yarn includes interstitial voids located between the splayed filaments of each of said yarns, and wherein said interstitial voids are enclosed within said matrix.

2. The mesh according to claim 1, wherein said matrix exteriorly surrounds said yarns and is formed of a material having a Young's modulus lower than the Young's modulus of the material forming the filaments of said yarns.

3. The mesh according to claim 2, wherein said matrix penetrates into said yarn to substantially fill the interstitial voids located therein.

4. The mesh according to claim 3, wherein said matrix is formed from a polymer selected from the group consisting of polyester, polypropylene, polyethylene, polyurethane, poly(meth) acrylate, and copolymers thereof.

5. The mesh according to claim 1, wherein said yarns are formed of a plurality of bi-component filaments each having a flexible core and a fusible sheath surrounding said core, and wherein said sheath has a fusing temperature lower than the melting temperature of said core whereby said sheaths fuse together to enclose said interstitial voids upon heating of said trellis.

6. The mesh according to claim 5, wherein said core is formed of a polyethylene terephthalate polyester and said sheath is formed of a polyethylene terephthalate/isophthalate copolyester.

7. The mesh according to claim 1, wherein said multifilament yarns overlap one another at regularly-spaced junctions to form said support trellis, and wherein said overlapping yarns are adhered to one another at said junctions to enhance ravel resistance of said mesh.

8. The mesh according to claim 1, wherein said matrix is drug permeable, and wherein a medicinal drug is incorporated into said matrix for release into the body of a patient after implantation of said mesh therein.

9. The mesh according to claim 1, wherein the mesh has a thickness less than about 0.20 millimeters.

10. The mesh according to claim 1, wherein said multifilament yarns have no twist imparted thereto.

11. A method of producing a soft and pliable surgical mesh exhibiting increased resistance to inhabitation of infectious matter from a support trellis formed of multifilament yarns having splayed filaments and defining interstitial voids between the splayed filaments of each yarn, comprising:
encapsulating said multifilament yarns within an infection-impervious matrix whereby the interstitial voids located between the splayed filaments of said yarns are enclosed within said matrix.

12. The method according to claim 11, wherein said encapsulating step includes the step of applying a resin to the exterior of said yarns prior to the forming of said trellis.

13. The method according to claim 12, wherein said resin is applied to the exterior of said trellis in sufficient quantity and for a sufficient period of time to allow said resin to penetrate into said yarn and substantially fill said voids.

14. The method according to claim 11, wherein said encapsulating step includes the step of applying a resin to the exterior of said yarns subsequent to the forming of said trellis.

15. The method according to claim 14, wherein said resin is applied to the exterior of said trellis in sufficient quantity and for a sufficient period of time to allow said resin to penetrate into said yarn and substantially fill said voids.

16. The method according to claim 11, wherein said yarns are formed of a plurality of bi-component filaments each having a flexible core and a fusible sheath surrounding said core, and wherein said encapsulating step includes the step of heating said trellis above the fusing temperature of said sheaths whereby said sheaths fuse together.

17. The method according to claim 16, wherein said fusing step is accomplished by application of thermal or light wave radiation to said trellis.

18. The method according to claim 11, further comprising the step of incorporating a medicinal drug into said matrix for release therefrom after implantation of said mesh into the body of a patient.

19. The method according to claim 11, further comprising the step of sealing said encapsulated trellis in a sterile package.

20. The method according to claim 11, further comprising the step of applying a compressive force to press the mesh to a desired thickness.

21. A method of repairing a damaged portion of a patient's body, comprising:

providing a soft tissue mesh, said mesh comprising a support trellis formed of multifilament yarns having splayed filaments and defining interstitial voids between the splayed filaments of each yarn, wherein said interstitial voids are encapsulated within an infection-impervious matrix whereby said mesh is soft and pliable while simultaneously exhibiting a resistance to inhabitation of infectious matter;

accessing said damaged portion of said body; and implanting said surgical mesh in said body to reinforce said damaged portion and allowing said mesh to assimilate into said body.

22. The method according to claim 21, wherein said yarns are formed of a plurality of bi-component filaments each having a flexible core and a fusible sheath surrounding said core, and wherein said providing step includes the step of heating said trellis above the fusing temperature of said sheaths whereby said sheaths fuse together to encapsulate said cores.

23. The method according to claim 21, wherein said matrix is drug permeable, and wherein a medicinal drug is incorporated into said matrix for release into the body of a patient after implantation of said mesh therein.

24. The soft tissue mesh of claim 1, wherein said trellis defines pores having a size in the range of 50 microns to 400 microns.

25. The soft tissue mesh of claim 7, wherein said trellis has a thickness in the range of 0.05 millimeters to 0.50 millimeters.

26. The soft tissue mesh of claim 7, wherein said trellis has a thickness less than 0.20 millimeters.

27. The soft tissue mesh of claim 26 wherein said trellis is sufficiently thin to permit insertion into a trocar having a diameter of about 5 millimeters or less.

28. The soft tissue mesh of claim 27, wherein said is mesh is heat conditioned for a sufficient time at a sufficient temperature to effectuate a shape-memory in an unfurled state.

29. The soft tissue mesh of claim 27, wherein said mesh includes yarns or filaments made from a shape-memory material.

* * * * *